US012620468B2

(12) United States Patent
Ghosh et al.

(10) Patent No.: US 12,620,468 B2
(45) Date of Patent: May 5, 2026

(54) PERSONALIZED LIVER CANCER TREATMENT

(71) Applicant: Hepatiq, Inc., Irvine, CA (US)

(72) Inventors: Dipankar Ghosh, Irvine, CA (US); John Carl Hoefs, Irvine, CA (US)

( * ) Notice: Subject to any disclaimer, the term of this patent is extended or adjusted under 35 U.S.C. 154(b) by 0 days.

(21) Appl. No.: 19/072,965

(22) Filed: Mar. 6, 2025

(65) Prior Publication Data

US 2025/0285727 A1     Sep. 11, 2025

Related U.S. Application Data

(60) Provisional application No. 63/562,626, filed on Mar. 7, 2024.

(51) Int. Cl.
| | |
|---|---|
| *G16H 20/10* | (2018.01) |
| *A61P 1/16* | (2006.01) |
| *G16H 30/20* | (2018.01) |
| *G16H 50/30* | (2018.01) |

(52) U.S. Cl.
CPC ................ *G16H 20/10* (2018.01); *A61P 1/16* (2018.01); *G16H 30/20* (2018.01); *G16H 50/30* (2018.01); *G01N 2800/085* (2013.01)

(58) Field of Classification Search
CPC ........ G16H 20/10; G16H 30/20; G16H 50/30; A61P 1/16; G01N 2800/085
See application file for complete search history.

(56) References Cited

U.S. PATENT DOCUMENTS

| | | | |
|---|---|---|---|
| 9,155,513 B2 | 10/2015 | Ghosh et al. | |
| 10,010,263 B2 * | 7/2018 | Cao | A61B 5/055 |
| 10,076,299 B2 * | 9/2018 | Ghosh | G06T 7/13 |
| 11,020,007 B2 * | 6/2021 | Kim | A61B 5/743 |
| 11,615,881 B2 | 3/2023 | Ghosh et al. | |
| 12,009,090 B2 | 6/2024 | Ghosh et al. | |
| 12,201,702 B1 * | 1/2025 | Lapotko | A61K 47/6929 |
| 2007/0136218 A1 * | 6/2007 | Bauer | G16H 50/20 |
| | | | 700/83 |
| 2008/0045609 A1 * | 2/2008 | DeVore | A61P 1/16 |
| | | | 514/789 |

(Continued)

FOREIGN PATENT DOCUMENTS

| | | | |
|---|---|---|---|
| EP | 2290611 A1 * | 3/2011 | A61B 5/055 |
| RU | 2673667 C2 * | 11/2018 | |

OTHER PUBLICATIONS

Tomassini et al., "Hepatic function assessment to predict post-hepatectomy liver failure: what can we trust? A systematic review," Updates in Surgery (2020) 72:925-938; https://doi.org/10.1007/s13304-020-00859-7. (Year: 2020).*

(Continued)

*Primary Examiner* — Jonathon A. Szumny
(74) *Attorney, Agent, or Firm* — CIONCA IP Law P.C.

(57) ABSTRACT

Systems and methods are provided for collecting and processing data from liver cancer patients that can be used to personalize treatment plans for these patients, including by determining and considering their liver functional reserve LFR. Specifically, systems and methods are provided for using fLV (functional liver volume) and PHM (perfused hepatic mass), before and after treatment, to determine personalized treatment plans and improve overall survival rates.

15 Claims, 7 Drawing Sheets

(56) References Cited

U.S. PATENT DOCUMENTS

| | | | | |
|---|---|---|---|---|
| 2008/0233583 | A1* | 9/2008 | Fisher | C12Q 1/6883 |
| | | | | 436/501 |
| 2010/0104540 | A1* | 4/2010 | Aloman | A61K 38/18 |
| | | | | 514/44 R |
| 2014/0147875 | A1* | 5/2014 | Everson | G01N 33/92 |
| | | | | 435/24 |
| 2016/0378950 | A1* | 12/2016 | Reiner | G16H 70/40 |
| | | | | 705/2 |
| 2018/0078313 | A1* | 3/2018 | Comaniciu | G16H 50/30 |
| 2018/0146880 | A1* | 5/2018 | Cao | G01R 33/5601 |
| 2019/0204402 | A1* | 7/2019 | Leporq | A61B 5/055 |
| 2019/0302460 | A1* | 10/2019 | Kaul | G02B 27/017 |
| 2021/0318274 | A1* | 10/2021 | Everson | H01J 49/0031 |
| 2022/0228192 | A1* | 7/2022 | Gaude | G01N 33/497 |
| 2022/0378786 | A1* | 12/2022 | Everson | A61K 31/40 |
| 2023/0383364 | A1* | 11/2023 | Li | G16H 50/30 |
| 2024/0062912 | A1* | 2/2024 | McRae | G01N 33/58 |
| 2024/0175881 | A1* | 5/2024 | McRae | A61B 5/7242 |

OTHER PUBLICATIONS

Sheung Tat Fan, "Liver functional reserve estimation: state of the art and relevance for local treatments," J Hepatobiliary Pancreat Sci (2010) 17:380-384; DOI 10.1007/s00534-009-0229-9. (Year: 2009).*

Kubota et al., "Measurement of Liver Volume and Hepatic Functional Reserve as a Guide to Decision-Making in Resectional Surgery for Hepatic Tumors," Hepatology vol. 26, No. 5, 1997. (Year: 1997).*

Tu et al., "Assessment of hepatic functional reserve by cirrhosis grading and liver volume measurement using CT," World J Gastroenterol Aug. 7, 2007; 13(29): 3956-3961; ISSN 1007-9327. (Year: 2007).*

Hyuna Sung, Jacques Ferlay, Rebecca L Seigel, Mathieu Laversanne, Isabelle Soerjomataram, Ahmedin Jermal Freddie Bray, Global Cancer Statistics 2020: GLOBOCAN Estimates of Incidence and Mortality Worldwide for 36 Cancers in 185 Countries, CA: A Cancer Journal for Clinicians, May 2021, vol. 71, Issue 3, United States. https://acsjournals.onlinelibrary.wiley.com/doi/10.3322/caac.21660.

American Cancer Society, Key Statistics About Liver Cancer, American Cancer Society, Feb. 11, 2025, United States, https://www.cancer.org/cancer/types/liver-cancer/about/what-is-key-statistics.html.

American Cancer Society, Can Liver Cancer Be Found Early?, American Cancer Society. Feb. 11, 2025, United States, https://www.cancer.org/cancer/types/liver-cancer/detection-diagnosis-staging/detection.html.

Mostafa Mohamed et al., Comparison of outcomes between SBRT, Yttrium-90 radioembolization, transarterial chemoembolization, and radiofrequency ablation as bridge to transplant for hepatocellular carcinoma, Advances in Radiation Oncology, Jan.-Mar. 2016, vol. 1, Issue 1, United States, https://www.advancesradonc. org/article/S2452-1094(15)00009-3/fulltext.

Fasih A. Ahmed, et al. Outcomes in elderly patients undergoing hepatic resection compared to ablative therapy for hepatocellular carcinoma, Journal of Surgical Oncology, Oct. 2023, vol. 128, Issue 5, United States, https://onlinelibrary.wiley.com/doi/epdf/10.1002/jso.27369.

Edward Kim, et al., Radiation segmentectomy for curative intent of unresectable very early to early stage hepatocellular carcinoma (RASER): a single-centre, single-arm study, The Lancet Gastroenterology and Hepatology, Sep. 2022, vol. 7, Issue 9, United States, https://www.thelancet.com/journals/langas/article/PIIS2468-1253(22)00091-7/abstract.

Chun-Yen Yu et. al., Yttrium-90 Radioembolization as the Major Treatment of Hepatocellular Carcinoma, Journal of Hepatocellular Carcinoma, Jan. 2023, United States, https://pmc.ncbi.nlm.nih.gov/articles/PMC9843618/.

* cited by examiner

101

202

707

807

1115  • Acquire Images

1116  • Retrieve Images

1117  • Retrieve Data

1118  • Obtain Therapy Plan

1119  • Get HEPATIQ Indices

1120  • Calculate Patient Trajectories

1121  • Construct Virulence/Reserve Matrix

1122  • Calculate LFR, PDV and DEF

1123  • Distribute HEPAPLAN Report

| VR Matrix | Virulence High | Virulence Low |
|---|---|---|
| Reserve High | DEF>1 | DEF=1 |
| Reserve Low | DEF=NA | DEF<1 |

PERSONALIZED LIVER CANCER TREATMENT

CROSS-REFERENCE TO RELATED APPLICATIONS

This application claims the benefit of U.S. Provisional Application No. 63/562,626, filed Mar. 7, 2024, which is hereby incorporated by reference, to the extent that it is not conflicting with the present application.

BACKGROUND OF INVENTION

1. Field of the Invention

The invention relates generally to technologies and methods for treating liver cancer patients. Specifically, the invention relates to data-driven systems and methods for designing personalized treatment plans for liver cancer patients, to improve their overall survival rates.

2. Description of the Related Art

Liver cancer (LC) is a deadly disease. Worldwide there were more than 900,000 new cases of liver cancer in 2020. The American Cancer Society estimates that about 41,000 new liver cancers are diagnosed in the U.S. each year and about 30,000 people die of the disease annually. Symptoms of liver cancer, such as abdominal pain, weight loss, nausea, ascites and jaundice are often not present until the later stages of the disease. For this reason, liver cancer is generally not detected early. Although there are several forms of liver cancer, the most common primary liver cancer is hepatocellular cancer (HCC).

Bridge Therapies

Liver transplantation (LT) has the greatest cure potential for LC patients. However, there is often a long wait (sometimes years) before a donor liver becomes available. Thus, LC patients are given palliative bridge therapies till a suitable donor liver becomes available. Bridge therapies include stereotactic body radiation therapy (SBRT), Yttrium-90 radioembolization (Y90), radiofrequency ablation (RFA), trans-arterial chemoembolization (TACE) and surgical resections. Response to the bridge therapy may be low and overall survival (OS) even lower due to recurrence of the LC. The number of patients who achieved a significant response after bridge therapy was 61% for TACE, 65% for SBRT, 67% for RFA, and 67% for Y90. Although, this supports the use of these interventions, it leaves open the question of OS. Significant portions of these patients did not survive even a short time after the intervention.

Overall Survival

Overall survival (OS) has been researched quite extensively. For example, in elderly patients with hepatocellular carcinoma (HCC), hepatectomy (OS 55%) beat ablation (OS 35%). Although the results are impressive for hepatectomy compared to ablation, it is not known why significant portions of both types of patients did not survive.

Therefore, there is a need to solve the problems described above by providing a system and method for improving outcomes for liver cancer patients.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect a system and a method are provided for collecting and processing data from liver cancer patients that can be used to personalize treatment plans for these patients, including by determining and considering their Liver Functional Reserve (LFR). Specifically, in an aspect, a system and a method are provided for using fLV (functional liver volume) and PHM (quantitative liver function), before and after treatment, to determine personalized treatment plans, including a personalized dose value (PDV) or a dose escalation factor (DEF). Thus, an advantage is the increase of the overall survival (OS) rates for the liver cancer patients. Another advantage is more data-driven and thus more control in designing the treatment plans for these patients and in predicting the outcomes of the ensuing treatments.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1:
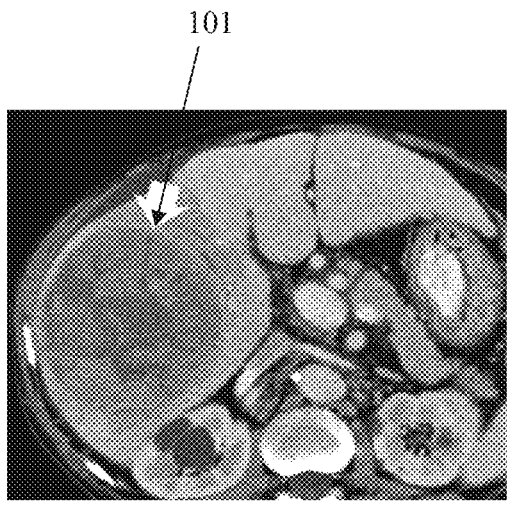
FIG. 1 is a CT image showing a large liver tumor.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some data, components or steps that are known in the art are not shown or described if they are not necessary for the invention to be understood by one of ordinary skills in the art.

Again, as indicated hereinabove, overall survival (OS) has been researched quite extensively. For example, in elderly patients with hepatocellular carcinoma (HCC), hepatectomy (OS 55%) beat ablation (OS 35%). Although the results are impressive for hepatectomy compared to ablation, it is not known why significant portions of both types of patients did not survive. While part of the reason may be the virulence of the cancer, inventor believes that important part of the reason may be that they did not have enough liver functional reserve to survive the treatment. Thus, use of a quantitative measure of liver functional reserve may improve outcomes for both hepatectomy and ablation procedures. The present disclosure provides a system and method for doing just that.

Overall survival rates can be improved by using strict patient selection criteria in an attempt to exclude patients who may not do well after the intervention. Research has indicated that radiation segmentectomy is efficacious as a curative treatment for well selected patients. Although encouraging, the strict selection criteria limit the patients who can benefit from the procedure. The selection criteria were: (1) no previous treatment for liver cancer, (2) tumor less than 3 cm, and (3) Child-Pugh (CP) score A-B7. Excluding patients with previous treatment for liver cancer is an indirect way to ensure they have enough liver functional reserve to survive the procedure. Small tumor size is another such indirect way to obtain favorable results. Excluding patients with Child-Pugh C is tantamount to excluding the most advanced cirrhotic patients where the incidence of hepatocellular carcinoma (HCC) is the highest. Instead of using such indirect and potentially less accurate means to select patients, the present disclosure provides system and method based on direct quantification of liver functional reserve, and thus, a more reliable patient selection approach that could save more lives. The direct quantification of liver functional reserve disclosed herein would permit the liver cancer treatment procedure to be more reliably applied to many more patients instead of a selected few.

Hereinbelow it is illustrated an exemplary system and method by using the Y90 intervention for the liver. It will be understood by those skilled in the art, that the system and method are not limited to Y90 treatments or to the liver. Besides Y90, the system and method can be used with other types of bridge therapies such as TACE, SBRT, RFA and surgical resection. The system and method can be used with other types of organs that may have long transplant wait times, such as for cancer of the pancreas, kidneys, lungs and heart.

Y90 is a popular intervention, but OS after Y90 therapy may be as low as 59% one year after the treatment. Thus, many of these patients are dying within 12 months after Y90 therapy. The cause of death may be due to the virulence of the cancer itself. It could also be due to inadequate pre-treatment liver functional reserve. The Y90 therapy involves a balancing act—the radiation dose administered should be enough for complete tumor necrosis but not so much that it destroys too many functioning liver cells. Thus, the patients who died within 12 months of Y90 therapy may have either (1) not received enough radiation dose to destroy all of the tumor, or (2) received too much radiation dose given the functional state of their livers. This balancing act is the purview of dosimetry which has its limitations. The present disclosure provides a novel system and method to personalize bridge therapy for liver cancer (LC) patients, so that the OS rates are significantly improved.

Current Dosimetry Practice

Dosimetry is performed with the aim of delivering the highest dose to the tumor while limiting the mean absorbed dose to non-tumor liver. The interventional radiologist will plan the rate of radioactive emissions (called "activity") upon the target tumor. Activity (A) is commonly measured as radioactive decays per second or Becquerel (Bq). In the United States, the Curie (Ci) is also commonly used to measure activity. A Ci is equal to 37 GBq. Dose (D) is the amount of energy J (measured in Joules) absorbed by the tumor per unit mass M (measured in kg). Dose is measured in units of Gray (Gy). Dose is directly proportional to the activity delivered to the tumor and inversely proportional to the mass of the tumor. So activity is delivery of radiation to tissue while dose is absorption of radiation per unit mass of tissue.

Figure 4:
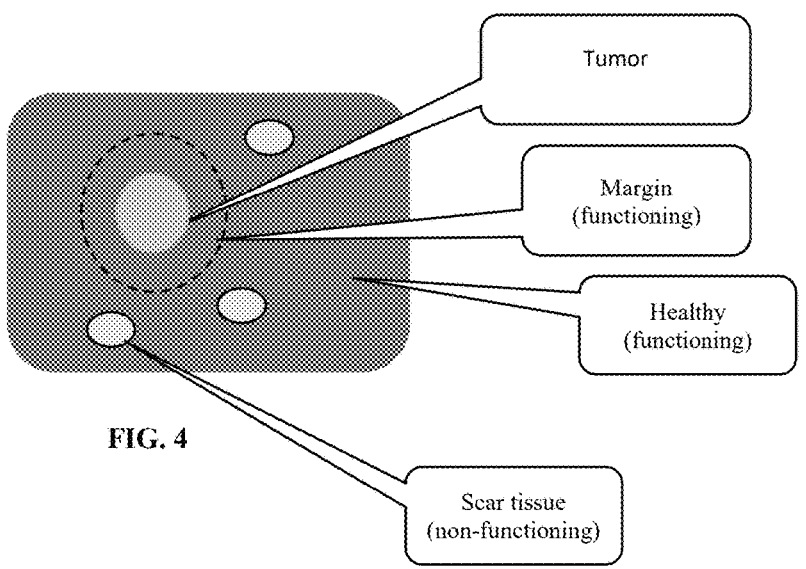
FIG. 4 is a schematic diagram of a liver cancer (LC) treatment.

The ratio of dose absorbed by the tumor ($D_T$) to the dose absorbed by non-tumor tissue ($D_N$) is known as the T/N ratio or $R_{T/N} = D_T/D_N$. It is an important treatment parameter used to plan LC therapy. $D_T$ and $D_N$ are calculated from the physical volume occupied by the tumor ($pV_T$) and non-tumor tissue ($pV_N$). These volumes are measured using CT or MRI imaging. The problem of course is that CT and MRI can only measure physical volumes which ignores the distinction between functioning and non-functioning tissue within the measured physical volume. Non-tumor regions of the liver may have scar tissue that is non-functioning (caused by cirrhosis or other liver diseases), as shown in FIG. 4. Including non-functioning non-tumor tissue as if it were functioning non-tumor tissue distorts the T/N ratio and can result in sub-optimal dose calculations. Depending on the type of tumor and the radioisotope used, the tumor may appear bright or dark. Those skilled in the art would know that the methods disclosed herein can be adapted to either type of tumor.

A three-compartment partition model is often used for dosimetry calculations. These compartments are: (1) the tumor, (2) non-tumor liver, and (3) lung tissue. The lung compartment comes into play as some of the activity escapes the liver and is shunted to the lungs. Dosimetry relies on multiple assumptions, including that each tumor and non-tumor compartment have homogenous Y90 distributions within themselves.

As known in the art, the dose absorbed by the tumor $D_T$ is directly proportional to the activity delivered to the tumor $A_T$ and inversely proportional to the mass of the tumor $M_T$, ie, $D_T = k*E*A_T/M_T$, where E=average energy emitted per radioactive decay transition and K is a constant. The total activity delivered is $A_{total}=A_T+A_N+A_L$ where $A_N$ is the activity to the non-tumor liver and $A_L$ is the activity shunted to the lungs.

The interventional radiologist uses practice guidelines to decide on the desired dose to the tumor $D_T$. They use practice guidelines to limit the dose to non-tumor liver tissue $D_N$. They may use other testing methods to estimate dose shunted to the lungs $D_L$. Knowing $D_T$, $D_N$, and $D_L$, the corresponding activities $A_T$, $A_N$, and $A_L$ can be calculated if the associated masses $M_T$, $M_N$, and $M_L$ are also estimated. Masses are estimated by calculating volumes and multiplying by an assumed density of the tissue (1.03 g/mL for liver and 1.00 g/mL for lung tissue). The total activity to be delivered to the patient is then calculated as $A_{total}=A_T+A_N+A_L$. Sometimes the lung shunt is ignored and the total activity delivered to the patient is simply $A_{total}=A_T+A_N$.

Typically, the non-tumor dose is limited to 70 Gy in the non-cirrhotic liver, and 40 Gy in the cirrhotic liver. This means that for cirrhotic patients with LC, a lower dose is used compared to non-cirrhotic patients with LC. Although this is a good first step, the systems and methods provided herein go much farther. In an aspect, the systems and methods provided herein can use liver functional reserve (LFR) to allow a continuous spectrum of limits and not simply arbitrary dose cut-offs, such as 40 Gy and 70 Gy.

Using LFR is important because, for example, all cirrhosis is not the same. Due to the liver's ability to regenerate and the body's ability to increase blood flow to the liver, some patients with cirrhosis have adequate liver functional reserve while others do not. Treating all cirrhotic patients alike may be a root cause of the low OS rates seen under current practice.

SPECT vs. CT/MRI

Current practice is to use CT or MRI to calculate the T/N ratios. These modalities provide high spatial resolution images of the physical anatomy but have no information about blood flow or organ function. FIG. 1 is a CT image showing a large liver tumor 101. Although the image has great clarity and detail, it has no information on the liver functional reserve. The anatomic physical volumes are entirely missing the blood flow rate factor. What matters is liver functional reserve which is related to blood flow.

Figure 2:
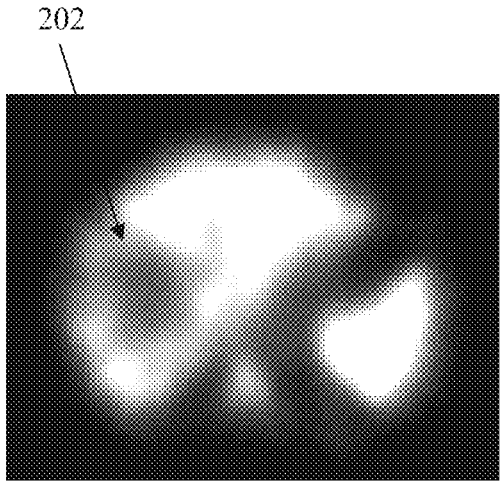
FIG. 2 shows a SPECT image of the liver after Y90 therapy.

SPECT provides relatively low spatial resolution but a wealth of information about blood flow and organ function. FIG. 2 shows a SPECT image of the liver after Y90 therapy. The dark region in the middle of the liver 202 indicates the large volume of liver tissue (tumor and non-tumor) destroyed by the radiation dose. SPECT can also distinguish between two types of non-tumor tissue: (1) healthy functioning tissue, and (2) non-functioning scar tissue caused by cirrhosis or other liver diseases.

SPECT functional volumes are different from the anatomic physical volumes provided by CT and MRI. In an aspect, the present disclosure provides a novel method to adjust the conventional dosimetry calculations to take into account an individual patient's functional liver volume and liver functional reserve.

Problems with Current Dosimetry Practice

Current dosimetry practice selects the dose based largely on the T/N ratio and the Child-Pugh (CP) score and some rules of thumb. It is not optimized or personalized based on the patient's liver functional reserve.

Tumor to Non-tumor Ratio

First, the use of the T/N ratio is a limitation of the current methodology. Dosimetry calculations are performed using physical tumor volume ($pV_T$) and physical non-tumor liver volume ($pV_N$). The volume measurements reflect the physical space occupied and are measured in cubic centimeters or similar units. Current dosimetry methodology conflates physical volumes with functioning tissue. Physical volume is not the same as functioning tissue, as a particular physical volume may contain both functioning and non-functioning (scar) tissue caused by cirrhosis of the liver.

Anatomical volumes calculated by CT or MRI estimate the physical space occupied by the tumor and non-tumor parts of the liver. That excludes the tumor volume from the liver volume but includes both functioning and non-functioning tissues in the non-tumor liver volume tissue. This inclusion of non-functioning liver tissue in the volume calculations as used currently in dosimetry, can lead to sub-optimal results, such as low OS rates.

Child-Pugh Score

Second, the use of the CP score in dosimetry is another limitation of the current methodology. The CP score is not a quantitative index, but instead a categorical score. The score is determined by assigning points to two clinical liver disease complications (encephalopathy and ascites), and three laboratory test results (Bilirubin, Albumin and Prothrombin Time/INR). Each of these five factors are assigned a score of 1 to 3 points for a minimum CP score of 5 points and a maximum CP score of 15 points. The total points determine the CP category:

A—Good hepatic function (5-6 points)

B—Moderately impaired hepatic function (7-9 points)

C—Advanced hepatic dysfunction (10-15 points).

Each of the five factors that make up the CP score are correlated and not independent of each other. They may indirectly relate to liver dysfunction but do not directly quantify liver functional reserve. Further, while the three laboratory test factors are objective, the two clinical factors are subject to interpretative variations. Thus, the use of anatomical volumes and the categorical CP scores for dosimetry calculations, and the virulence of the cancer are likely factors leading to a wide divergence of outcomes and low OS for LC bridge therapy.

Personalized Dosimetry

This applicant manufactures a patented software product—HEPATIQ®—which is used for the diagnosis of liver disease severity and portal hypertension, as further described in applicant's patents, U.S. Pat. Nos. 9,155,513, 10,076,299, 11,615,881 and 12,009,090 ("applicant's patents"), which are hereby incorporated by reference to the extent they do not conflict with the present application.

For the HEPATIQ® test, the patient is injected with a standard low dose Technetium-99m sulfur colloid solution and a 20 minute SPECT scan is performed. HEPATIQ® uses ratiometric and concentration algorithms and technologies to overcome any limitations due to the larger SPECT voxel size compared to CT or MRI, as disclosed in applicant's patents. As further disclosed in applicant's patents, HEPATIQ® calculates several indices of liver disease including perfused hepatic mass (PHM), functional liver volume (fLV), functional spleen volume (fSV), and hepatic activity index (HAI).

In an aspect, the present disclosure provides a system and method of using fLV (functional liver volume) and PHM (perfused hepatic mass) to supplant the T/N ratio (physical volume ratio) and the CP score (subjective categorical score) in dosimetry calculations for LC treatment. The disclosed system and method can allow SPECT scans to be used for a more effective personalized planning of bridge treatments for LC patients.

In an aspect, the present disclosure provides a new LC therapy planning software (HEPAPLAN™) that can calculate a personalized dose value (PDV) for LC treatment for a particular patient independent of current dosimetry methodologies. Furthermore, in another aspect, HEPALAN™ can augment current dosimetry methodologies by calculating a dose escalation factor (DEF). In an aspect, both PDV and DEF may take account of the virulence (V) of the cancer in addition to the liver functional reserve LFR. These two capabilities can provide true personalized LC therapy, where for example patients with adequate liver functional reserve receive the most aggressive dosing, while those with inadequate liver functional reserve receive the least aggressive dosing. The PDV calculated by HEPAPLAN™ provides an optimal dose given the patient's liver functional reserve while the DEF provided by HEPAPLAN™ can allow for adjusting (up or down) the dose calculated by using current dosimetry methodologies. This can improve OS prospects for the entire spectrum of patients. The DEF provides the interventional radiologist a way to try out and learn the new methodology without discarding their current methodology. It is expected that as customers see the benefits of the new methodology, they will discard the old methodology and simply switch to using PDV to get better OS for their patients.

Novel Methodologies Provided

Calculating Liver Function Reserve

HEPAPLAN™ includes a novel method of calculating pre-therapy LFR. The method uses functional parameters PHM and fLV to capture the combined effect of the remaining functional tissue and the blood flow through them.

HEPAPLAN™ calculates a quantitative LFR=ψ(PHM, fLV) where ψ( ) is a composite function of the independent variables PHM and fLV. ψ( ) may be determined by validation against a known data set.

Normal PHM is 100 to 110. Low PHM<75 is a prognosticator of poor liver disease outcomes regardless of the presence or absence of liver cancer. Normal fLV is 7 to 12. Small fLV<5 is also a prognosticator of poor liver disease outcomes. Combining the two parameters provides a full quantification of LFR.

In its simplest form, LFR=K*fLV*PHM, where K is a normalization vector. At is simplest form K is a constant. However, K may depend on patient characteristics, such as gender, height, weight, age, biomarkers and genetic factors. Those skilled in the art would know that data cluster analysis may be used to determine a vector K that accounts for patient characteristics.

Furthermore, K can be determined using an AI (artificial intelligence) module or as a deep learning neural network that improves over time as more customers use HEPAPLAN™ and additional data is accumulated.

Figure 3:
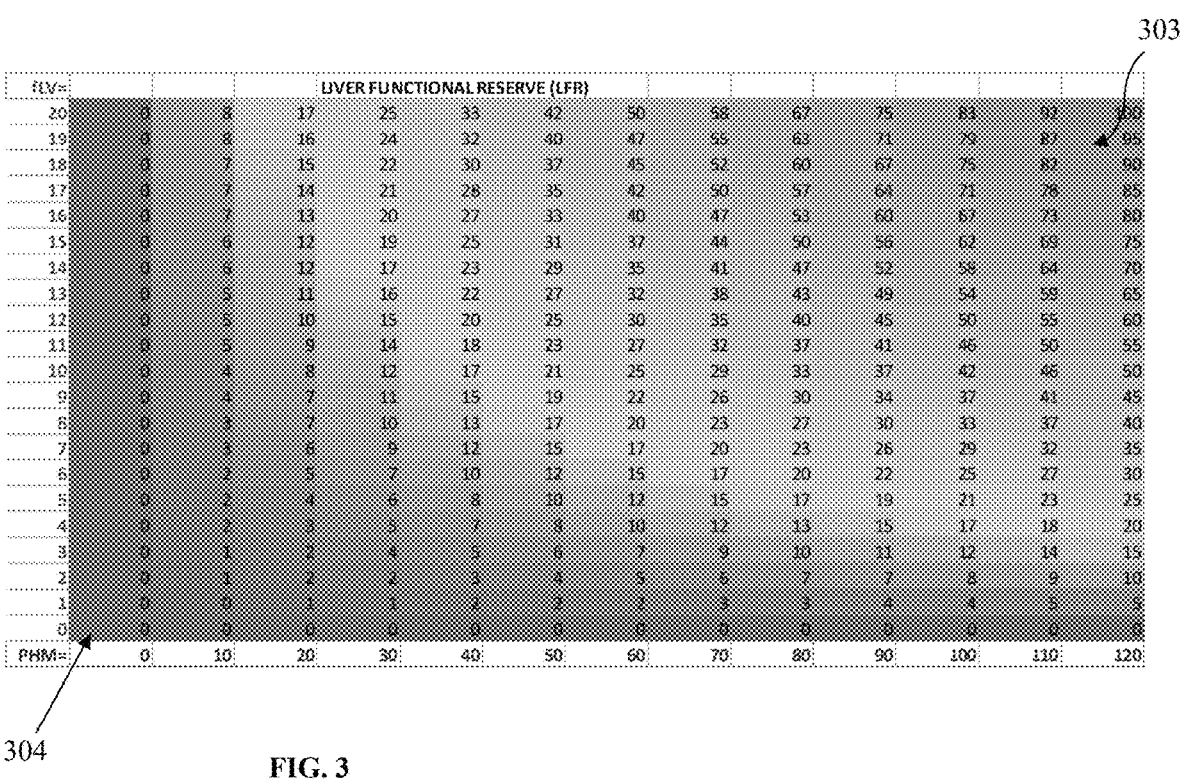
FIG. 3 is a chart showing a simplified Liver Functional Reserve (LFR), according to an aspect.

FIG. 3 plots fLV (y-axis) against PHM (x-axis) and shows corresponding LFR values using the simple linear form LFR=K*fLV*PHM with K a constant equal to 0.0416. The medium-dark regions 303 indicate patients with large LFR who would tolerate aggressive dosing or dose escalation well while the dark regions 304 indicate patients with low LFR who may be better served with dose de-escalation or alternate therapies. Their low LFR may also be used to justify moving those patients up in priority on the liver transplant waiting list.

When HEPAPLAN™ is used by itself (without conventional dosimetry) the method can be used to compute a Personalized Dose Value (PDV). When HEPAPLAN™ is used to augment conventional dosimetry, the method can include calculating a dose escalation factor DEF.

If DEF=1, the dose calculated by conventional dosimetry may be used. If DEF>1, the dose calculated by conventional dosimetry can be escalated by the DEF. If DEF<1, the dose calculated by conventional dosimetry can be de-escalated by the DEF. Thus, while current dosimetry calculations are performed using anatomic volumes, the personalization of the therapy can be performed using the functional liver volume fLV and perfused hepatic mass PHM indices provided by HEPATIQ®.

Calculating Dose Limits Using LFR

Figure 5:
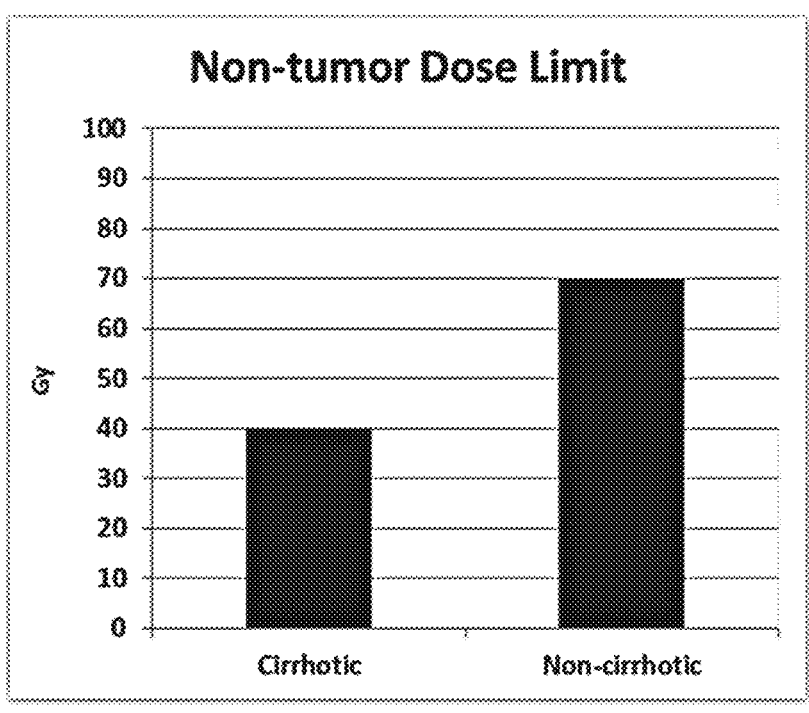
FIG. 5 is a chart showing non-tumor dose limits according to the conventional method.
Figure 6:
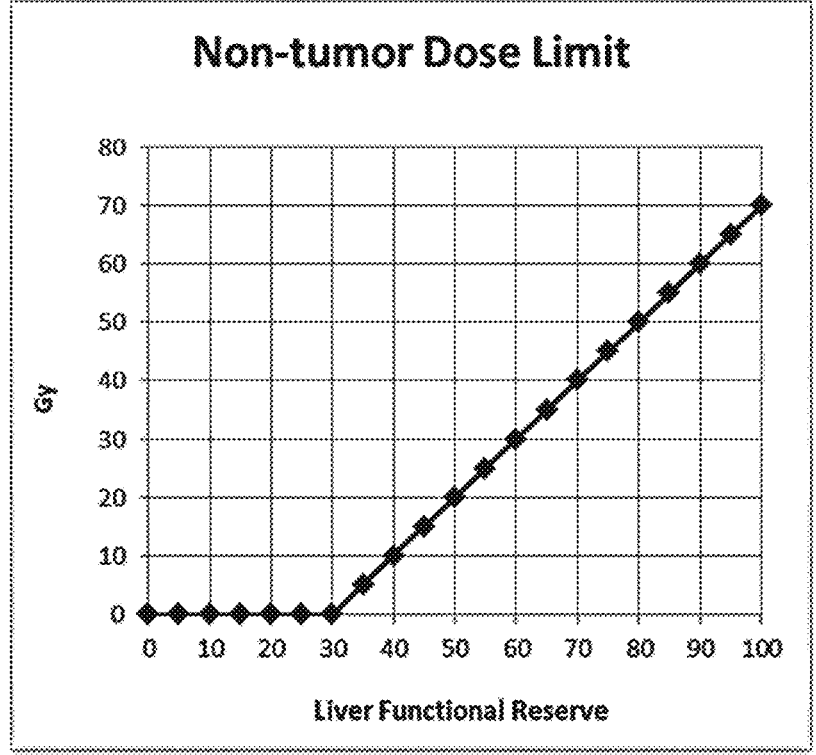
FIG. 6 is a chart showing non-tumor continuous dose limits according to the disclosed method.

Instead of limiting the non-tumor dose to 70 Gy in the non-cirrhotic liver, and 40 Gy in the cirrhotic liver, as shown in FIG. 5, the method disclosed herein using the LFR allows a continuous spectrum of limits, as illustrated in FIG. 6, showing a simple linear dependency between the non-tumor dose limit and the LFR. The coefficients of the linear dependency may be determined by validation against a known data set. Those skilled in the art would know that other non-linear relationships can be used and AI based deep learning networks can be employed to improve the relationship as more customers use HEPAPLAN™.

In current conventional dosimetry practice, cirrhotic patients with LC get a lower dose as compared to non-cirrhotic patients with LC. Although this is a good first step, the systems and methods provided herein go much farther. Again, the disclosed systems and methods use LFR that may allow a continuous spectrum of limits and not simply arbitrary dose cut-offs, such as 40 Gy and 70 Gy. By way of illustration, per FIG. 6, patients with LFR≥100 are allowed a non-tumor dose limit of 70 Gy. Patients with 95≤LFR<100 are allowed a non-tumor dose limit of 65 G. Patients with 90≤LFR<95 are allowed a non-tumor dose limit of 60 G and so on, 'till the point of no dosing is reached.

Calculating T/N Ratio Using Functional Volumes

T/N ratio is re-calculated using functional volumes obtained from SPECT rather than anatomic volumes obtained from CT or MRI. The functional liver volume (fLV) is calculated as taught in U.S. Pat. Nos. 9,155,513 and 10,076,299. The tumor volume (TV) is calculated as taught in U.S. Pat. Nos. 11,615,881 and 12,009,090. The T/N ratio $R_{T/N}$ is calculated as TV/fLV. These SPECT functional volumes (fV) differ from the physical volumes (pV) that result from using CT or MRI. CT and MRI end up including non-functioning tissue in their volume calculations because they take up physical space. SPECT ends up naturally excluding non-functioning scar tissue in its volume calculations because non-functioning tissue does not take up the radioisotope and thus does not contribute to the emissions. Including non-functioning non-tumor tissue as if it were functioning non-tumor tissue distorts the T/N ratio and can result in sub-optimal dose calculations and lead to low OS. The methods disclosed here avoid those problems.

Calculating PDV

In conventional dosimetry, the T/N ratio is calculated as:

$$R_{T/N}=D_T/D_N=(A_T/M_T)/(A_N/M_N)$$

where $D_T$ is the dose absorbed by the tumor, $D_N$ is the dose absorbed by non-tumor tissue, $A_T$ is activity to tumor, $A_N$ is activity to non-tumor tissue, $M_T$ is the mass of the tumor, and $M_N$ is the mass of the non-tumor tissue.

The activity delivered to the patient is calculated as:

$$A_{total}=K*D_N*[R_{T/N}*M_T+M_N]$$

where K is a constant that includes the estimated lung shunt, $D_N$ is dose to non-tumor liver tissue.

With the methods disclosed herein, the $D_N$ is replaced with a personalized dose value (PDV) that depends on the liver functional reserve (LFR) and virulence (V):

$$PDV=\varphi(LFR,V)$$

The activity delivered to the patient is then calculated as $$A_{total}=k*PDV*[R_{T/N}*M_T+M_N]$$

In its simplest form, the personalized dose value PDV is a linear function of LFR and V:

$$PDV=\varphi(LFR,V)=\alpha*LFR+\beta*V+\gamma$$

where $\alpha$, $\beta$ and $\gamma$ are standardization constants that (optionally) includes the estimated lung shunt. The standardization constants may be determined by validation against a known data set. Those skilled in the art would know that other non-linear relationships can be used and AI based deep learning networks can be employed to improve the relationship as more customers use HEPAPLAN™.

Calculating DEF

The DEF is calculated as $DEF=PDV/D_N$. As an example, if conventional dosimetry suggests $D_N=40$ Gy, and the methodology disclosed here indicates PDV=50 Gy, then DEF=50/40=1.2. If DEF>1, the dose calculated by conventional dosimetry can be escalated by the DEF. If DEF<1, the dose calculated by conventional dosimetry can be de-escalated by the DEF.

Calculating Margins

Once $A_{total}$ is calculated, the margins it will generate can be predicted using standard radiation decay calculations.

Predicting Therapy Outcomes

The present disclosure also provides a system and method for predicting liver disease progression trajectories, likelihood of LC occurring, and outcome of LC treatment for individual patients. Trajectories are extrapolations of the trend in serial studies shown by dotted lines ending in an arrow in FIGS. 7, 8 and 9. Extrapolations are performed using the most recent two or three studies depending of the number of previous studies available. Linear extrapolations are shown. Those skilled in the art would know that other more complex extrapolation techniques can be used. Exemplary system and method are described herein for using three different disease progression trajectories. These teachings use exemplary patient data and are not limiting. Those skilled in the art will recognize that a very large number of classifiable trajectories may be used to predict disease progression trajectories for individual patients.

Patient 1 (Tumor Recurrence in 8 Years)

Figure 7:
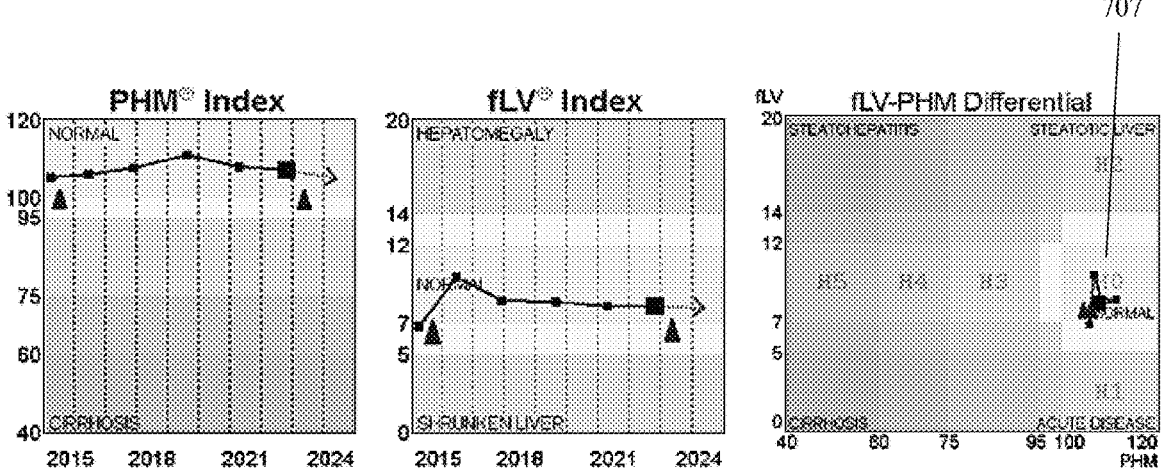
FIG. 7 depicts charts showing tumor recurrence in a first patient in eight years.

As an example, in FIG. 7, Patient 1 had a 2 cm HCC in early 2015 which was treated with microwave ablation (shown by the triangles). The tumor re-occurred about 8 years later and was again treated with microwave ablation. The virulence vector for the HCC was low. The patient had normal perfused hepatic mass (PHM) and normal functional liver volume (fLV) at the time of each treatment, so the good outcome may be predictable for each treatment. The fLV-PHM differential shows a trajectory that remains in the normal region 707 throughout this time period. The dose parameters determined by current dosimetry practice may be adequate for each treatment and HEPAPLAN™ may recommend no dose adjustment, i.e., DEF=1.

Patient 2 (Tumor Recurrence in 4 Months Followed by Death)

Figure 8:
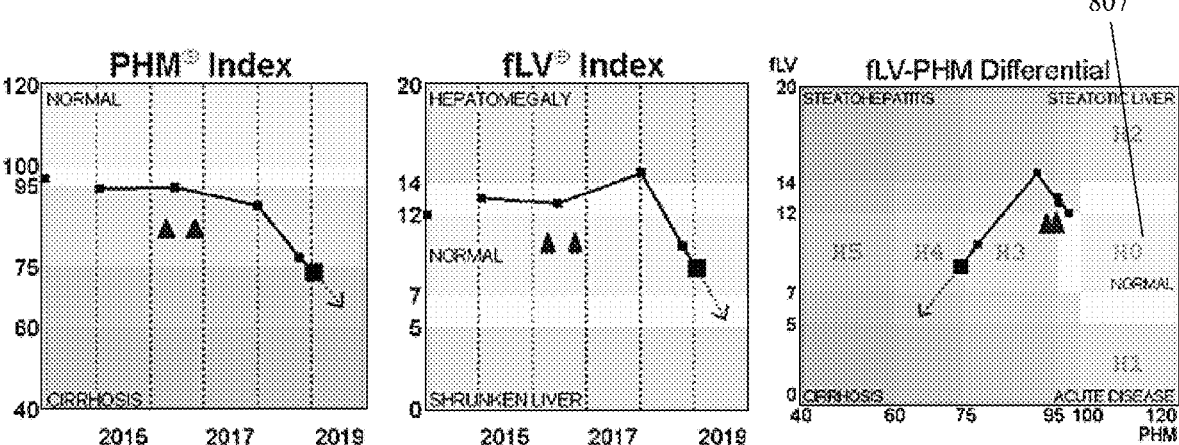
FIG. 8 depicts charts showing tumor recurrence in a second patient in four months followed by death.

In another example, in FIG. 8, Patient 2 had a 4 cm HCC (double the size of Patient 1), which was treated with trans-arterial chemoembolization (TCA) in April 2016 (left triangle). The tumor returned quickly, and the patient was treated with Y90 radioembolization just four months later in August 2016 (right triangle). However, the patient passed away about two years later. The fLV-PHM differential shows a rapidly deteriorating trajectory outside the normal region 807. This may be due to the virulent nature of the patient's HCC and the amount of cancer cells missed by the Y90 treatment.

Given that the patient had only moderately reduced liver function, they may have tolerated a higher dose of the Y90. The higher dose may have missed fewer cancer cells, and the patient may have survived longer. HEPAPLAN™ may have recommended dose escalation, i.e., DEF>1.

Patient 3 (Tumor Recurrence in 4 Months but Surviving)

Figure 9:
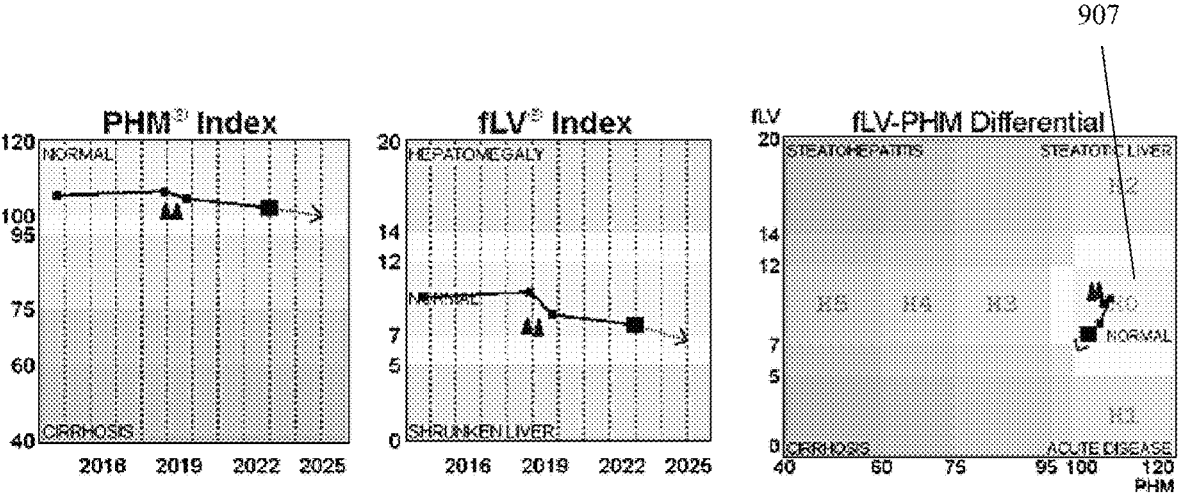
FIG. 9 depicts charts showing tumor recurrence in a third patient in four months but surviving.

As another example, in FIG. 9, Patient 3 had a 2.5 cm HCC (a little larger than Patient 1) which was treated with Y90 in December 2018. However, the Y90 was not entirely successful, and tumor reoccurred quickly. Four months later, in April 2019 a RFA was successfully performed and follow up imaging showed no sign of tumor. The fLV-PHM differential shows again a trajectory in the normal region 907.

Since the patient had normal liver function, they may have tolerated a higher dose of Y90. If the Y90 dosage had been personalized based on the patient's residual liver function, the RFA treatment just four months later may not have been needed. HEPAPLAN™ may have recommended dose escalation for the Y90, i.e., DEF>1.

It should be understood that the systems and methods described herein can be implemented by a computer system comprising computer hardware, peripheral devices and software programs. The computer system may include one or more physical computing devices, which may be geographically dispersed or co-located.

HEPAPLAN System

Figure 10:
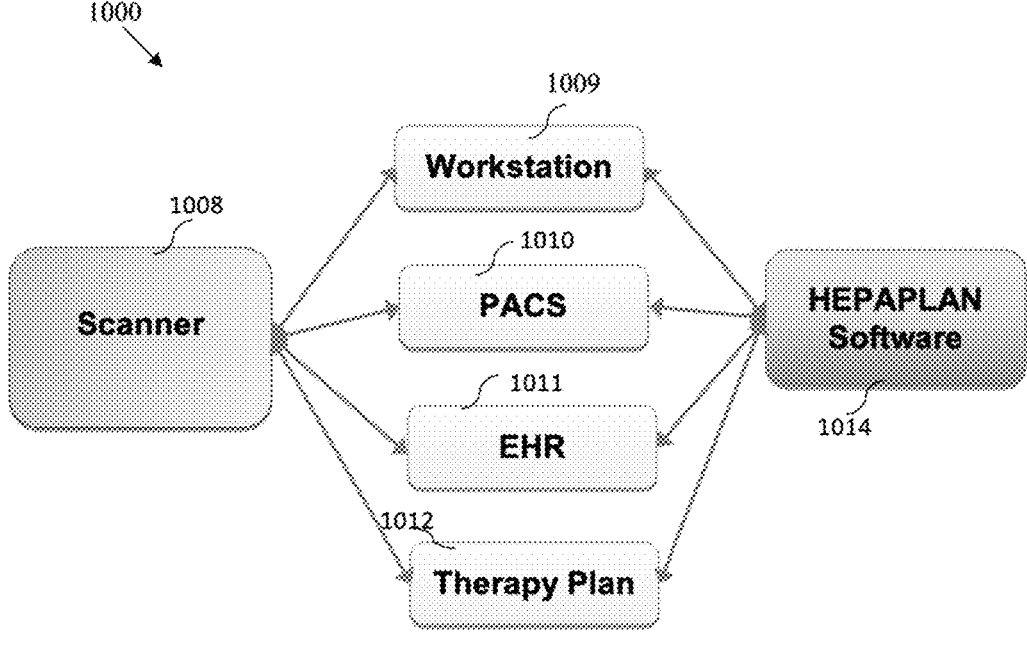
FIG. 10 is a block diagram of an exemplary system for determining personalized treatment plans for liver cancer patients, according to an aspect.

FIG. 10 is a block diagram of an exemplary HEPAPLAN™ system. In an example, all of the shown blocks are connected to each other via a network, as suggested by the arrows between them.

Scanner

The system 1000 can include a scanner 1008, such as a Single Photon Emission Computed Tomography (SPECT) scanner, or other functional scanner technologies such as PET, PET/CT, fCT, fMRI, etc. Exemplary SPECT and hybrid SPECT/CT scanners are commercially available from several manufacturers such as General Electric Healthcare. The SPECT scanner can be used to take liver images of the patient. The hybrid SPECT/CT scanners can be used to obtain both physical and functional volumes of the patient's liver and tumor.

Workstation

The system 1000 can include a workstation 1009 for interfacing to the HEPAPLAN™ software or for directly running the HEPAPLAN™ software. As an example, the workstation 1009 may be a personal computer running the Windows operating system. The system 1000 may include other computing elements, including personal computers, tablet computers, smart phones, scanners, and/or the like. The system 1000 may utilize other operating systems including Apple and Android operating systems, and/or the like.

PACS

The system 1000 can include a Picture Archiving and Communications Systems (PACS) 1010. Liver images of the patient taken on the Scanner 1008 can be transferred to the PACS 1010 for storage. Exemplary PACS are commercially available from vendors such as Mckesson Radiology. The system 1000 may include, and/or have access to (e.g., be in communication with), other image storage devices or systems, which can include the scanner or any computer readable storage medium and/or device (or collection of data storage mediums and/or devices), including, but not limited to, one or more memory devices that store data, including without limitation, dynamic and/or static random-access memory (RAM), programmable read-only memory (PROM), erasable programmable read-only memory (EPROM), electrically erasable programmable read-only memory (EEPROM), optical disks (e.g., CD-ROM, DVD-ROM, etc.), magnetic disks (e.g., hard disks, floppy disks, etc.), memory circuits (e.g., solid state drives, random-access memory (RAM), etc.), and/or the like.

EHR

The system 1000 may communicate with a server (not shown) via a network. The network can include any one or more communications networks. The network can include a plurality of computing devices configured to communicate with one another. The network can include the Internet. The network may be any combination of local area network ("LAN") and/or a wide area network ("WAN"), or the like. Accordingly, various computing devices can communicate with one another directly or indirectly via any appropriate communications links and/or networks (e.g., one or more communications links, one or more computer networks, one or more wired or wireless connections, the Internet, any combination of the foregoing, and/or the like).

The server may comprise one or more computing devices including one or more hardware processors. The server may comprise program instructions configured to cause the server to perform one or more operations when executed by the hardware processors. The server may include, and/or have access to (e.g., be in communication with) a storage device or system which can include any computer readable storage medium and/or device (or collection of data storage mediums and/or devices), including, but not limited to, one or more memory devices that store data, including without limitation, dynamic and/or static random-access memory (RAM), programmable read-only memory (PROM), erasable programmable read-only memory (EPROM), electrically erasable programmable read-only memory (EE-PROM), optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. In some implementations, the server may host a database which can be any data structure (and/or combinations of multiple data structures) for storing and/or organizing data, including, but not limited to, relational databases (e.g., Oracle databases, PostgreSQL databases, MySQL databases and the like), non-relational databases (e.g., NoSQL databases, and the like), in-memory databases, spreadsheets, as comma separated values ("CSV") files, extensible markup language ("XML") files, TeXT ("TXT") files, flat files, spreadsheet files, and/or any other widely used or proprietary format for data storage. Databases can be stored in one or more data stores. In some implementations, the server may include and/or be in communication with a hosted storage environment that includes a collection of physical data storage devices that may be remotely accessible and may be rapidly provisioned as needed (commonly referred to as "cloud" storage). In some implementations, the server(s) may comprise and/or be in communication with an Electronic Health Records (EHR) system 1011. And EHR can comprise a proprietary EHR. An EHR can store data such as patient data, including demographics, clinical indications, medications, laboratory results, history, etc. Exemplary EHR are commercially available from vendors such as EPIC.

Therapy Plan

The system 1000 can include a surgical, intervention or therapy planning system 1012. A surgeon or interventional radiologist can use the planning system to plan the therapy. The system 1000 can use this plan information for providing personalization parameters and predicting the outcome of the therapy, as disclosed herein.

For example, pre-operative planning systems, such as 3DVAPS, allow intuitive display of the spatial relationship between tumors and the surrounding tissue structures. It helps calculate the tumor volume, plan ablation parameters and needle insertion directions, predict ablation heat fields, enhance safety and effectiveness, and reduce complications.

HEPAPLAN™ Software

The system 1000 can include a computer-readable storage medium 1014, wherein the computer readable storage medium has program instructions embodied therewith, such as the HEPAPLAN™ Software, the program instructions executable by one or more processors to cause the one or more processors to perform operations comprising one or more aspects of the above- and/or below-described implementations (including one or more aspects of the appended claims). The Software may run on a Workstation 1009 or in the cloud, for example. The HEPAPLAN™ Software can determine personalized LC therapies and predicts outcomes as disclosed herein. The results can be included in a report. As a non-limiting example, the HEPAPLAN™ Software may comprise several sub-programs:

i. Workstation interface, ii. PACS Interface, iii. EHR Interface, iv. HEPATIQ® interface (not needed for standalone operation), v. HEPAPLAN™ Analyzer (performs all calculations for the HEPAPLAN™ as disclosed herein), and vi. HEPAPLAN™ Reporter (prepares report for distribution).

The Workstation and PACS Interfaces can transfer liver images to the HEPAPLAN™ Software and receive back the HEPAPLAN™ Reports. The EHR Interface can transfer patient data to the HEPAPLAN™ Software and receive back the HEPAPLAN™ Reports. The optional HEPATIQ® Interface can provide the liver diagnostic indices to the HEPAPLAN software.

The HEPAPLAN™ Analyzer can process liver images and determine personalized LC therapies including LFR, PDV, DEF pre- and post-therapy, as disclosed herein. The HEPAPLAN™ Reporter can generate the HEPAPLAN™ Report. One of skill in the art will understand that different sub-programs may be used, or no sub-program may be used.

HEPAPLAN™ Method

Figure 11:
FIG. 11 is a flowchart showing an exemplary method for determining personalized treatment plans for liver cancer patients, according to an aspect.

FIG. 11 is a flowchart of an exemplary HEPAPLAN™ method showing the exemplary steps 1115-1123. References will be made below to FIG. 10 as well, to help understand the exemplary method depicted in FIG. 11.

Acquire Images

In this step 1115, as an example, the patient is injected with a sulfur colloid (SC) solution labeled with a radionuclide such as Technetium-99 metastable (T99m) and SPECT images acquired of the liver using the Scanner 1008 (FIG. 10). One of skill in the art will understand that other suitable solutions and radioisotopes or radionuclides may be used. One of skill in the art will also understand that other image views may be employed, such as, anterior, posterior, oblique, sagittal, coronal, reformatted, secondary captures, or derived images. It is also understood that raw scanner data can be employed rather than image data.

The acquired images may be stored on the scanner temporarily and transferred to PACS 1010 for long-term storage. The archived images may or may not be encrypted. As an example, the method may include analyzing images in Digital Imaging and Communications in Medicine (DI- COM) format. However, one of skill in the art will understand that images may be in alternate formats.

Retrieve Images

The method can include automatically retrieving the SPECT liver images (step 1116) from the PACS 1010 by the Workstation 1009. For example, images can be retrieved using the DICOM protocols, although other protocols may be used as well. Images may also be retrieved by the Workstation 1009 directly and automatically from the Scanner 1008 or from other archival devices, such as a CD, DVD, USB Stick, workstation, server, network, the internet, and/or the like. Images may be automatically or manually transmitted from the source (e.g., Scanner or archival device) to the Workstation 1009 rather than being retrieved by the Workstation from the source. In an example, the HEP-APLAN™ software may run on the cloud and retrieval of images may be done through secure internet connections and firewalls.

Retrieve Data

The method can include step 1117 for automatically retrieving patient data, including demographics, clinical indications, medications, history, laboratory results, physician orders, etc. from the EHR 1011 by the Workstation 1009. For example, data can be retrieved using the HL/7 protocols, although other protocols may be used. The data may also be retrieved directly from the patient or from other information sources. The data may be automatically or manually transmitted from the source to the Workstation 1009 rather than being retrieved by the Workstation 1009 from the source.

Obtain Therapy Plan

The method can also include step 1118 for automatically obtaining the parameters of the planned surgery or intervention. These may be different for each planned procedure. Planning hepatic resection requires consideration of the nature of the lesion and its location within the liver, the patient's anatomy, and the quality and volume of the liver tissue that will remain after resection. For a Y90 procedure this may include the angiography information for delivery of the radioisotope and the planned dose. For an SBRT, this may include information on patient immobilization, lesion localization and the number of fractionated doses delivered. HEPAPLAN™ can use this information in its calculations. It is understood that although details may be different for each type of intervention, the concepts of Liver Functional Reserve as applicable can be used to predict the likelihood of liver failure post-intervention.

Get HEPATIQ® Indices

The method can include step 1119 of using the patented HEPATIQ® software to calculate the HEPATIQ® indices, i.e., PHM and fLV if HEPAPLAN™ is added to an existing HEPATIQ® customer. If serial studies are available, the HEPATIQ® indices can be calculated for each study in the series.

Calculate Patient Trajectories

Figures 12, 13:
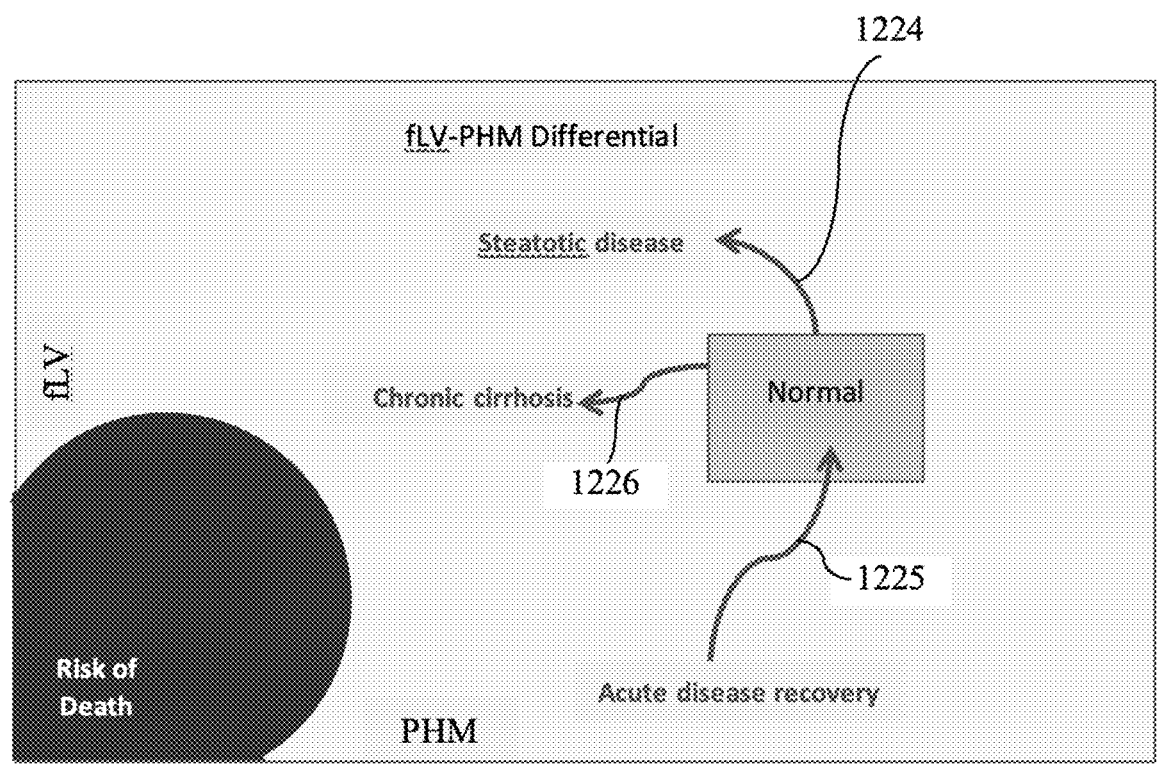
FIG. 12 is an fLV to PHM differential graph which shows fLV (vertical axis) plotted against PHM (horizontal axis).
FIG. 13 shows a simplified categorical VR matrix with two categories (low and high) for both Virulence and Reserve.

FIG. 12 is an fLV to PHM differential graph which shows fLV (vertical axis) plotted against PHM (horizontal axis). Normal is a small region shown boxed in the upper right of the differential graph. Patients in the normal region have high liver functional reserve. Patients on the lower left corner have low fLV and low PHM. Those patients have low liver functional reserve. As their liver disease progresses, they are likely to do poorly regardless of whether later on liver cancer develops. Each SPECT study performed on the patient provides a pair of fLV and PHM values which can be plotted on the 2D differential graph. These series of points define a trajectory for the progression of chronic liver disease. If the patient develops LC it may alter the trajectory. Also, the outcome of LC therapy may depend on how fast they are deteriorating on the trajectory. FIG. 12 shows patient trajectories over time on serial studies for three different types of liver diseases—chronic cirrhosis, steatotic disease and acute disease. The method can include analyzing these trajectories and the rates of traversal through them to predict patient outcomes. Outcomes can include both the disease end point and the timeframe for reaching that end-point. Traversal rate is a measure of the movement on the differential graph per unit time.

The trajectories can be coded and labelled into a multitude of disease progression categories. These can be used for further personalized monitoring and management of the patient. As an example, steatotic liver disease will tend to increase fLV but leave PHM normal at least initially. This is shown in first arrow 1224 going north out of the normal region. If the steatotic disease progresses to steatohepatitis, PHM will start decreasing and fLV will shrink and the trajectory will bend down towards the southwest corner. For non-steatotic liver disease, fLV does not increase, but PHM may start decreasing if the liver is nor regenerating or blood flow is not increasing to compensate for liver damage. This is shown by the second arrow 1226 going west out of the normal region. If the chronic disease progresses to hepatitis and cirrhosis, PHM will start decreasing and fLV will shrink and the trajectory 1226 will bend down towards the southwest corner. In case of acute disease, PHM will appear normal or near normal, but fLV will be diminished. If the acute disease is properly treated, the patient will recover back to normal. This is shown by the third arrow 1225 heading north towards normal.

Construct Virulence/Reserve Matrix

The method can include step 1121 of constructing a multi-dimensional Virulence/Reserve (VR) matrix containing cancer virulence and liver functional reserve data. An example of such matrix is shown in FIG. 13 indicating DEF values. A similar matrix could be constructed for PDV.

The virulence (V) can be approximated with standard cancer staging scales, such as the American Joint Committee on Cancer [TNM] system, which is based on three key pieces of information: (1) The extent (size) of the tumor [T], (2) The spread to nearby lymph nodes [N], and (3) the spread (metastasis) to distant sites [M]. It is understood that other scales may be used. Furthermore, replication rates of the cancer cells may be substituted if known.

The liver functional reserve (LFR or R) may be a combination of PHM and fLV based on an initial database of liver cancer patients. This can be updated using a learning algorithm as more customers use HEPAPLAN™. This may also be adjusted based on the patient's trajectory and the estimated time of the intervention.

FIG. 13 shows a simplified categorical VR matrix with two categories (low and high) for both Virulence and Reserve. One of skill in the art will understand that finer categories may be used. Also, the categories may be replaced with continuous variables.

Calculate LFR, PDV and DEE

In step 1122, LFR, PDV and/or DEF may be determined as disclosed hereinabove. Also, in an example, a dose escalation factor DEF may be selected. FIG. 13 shows exemplary general guidelines for DEF for the simplified categorical VR matrix. If DEF=1, the method may include recommending unchanged use of current dosimetry calculations. If DEF>1, the method may include recommending escalation of the dose calculated by current dosimetry. If DEF<1, the method may include recommending de-escalation of the dose calculated by current dosimetry. If DEF=NA, the method may include not making a recommendation and leaving the matter to patient/physician choice.

The initial DEF values may be based on a retrospective analysis of the applicant's own database of patients. A neural network-based learning system has been developed, which may gather data from the usage of the systems and methods as described herein to refine the DEF values over time as more customers use the product.

Distribute HEPAPLAN Report

The method can include step 1123 of preparing and distributing a comprehensive HEPAPLAN™ Report to the Workstation 1009, PACS 1010, EHR 1011 and/or Therapy Planning Systems. As a non-limiting example, the report can include information such as:

Patient Information
    Therapy Plan
    Pre-therapy PHM, fLV, LFR, PDV and DEF
    Predicted post-therapy PHM, fLV and LFR
    Post-therapy complications (ascites, encephalopathy, and
        variceal bleeding)
    Risk of post-therapy liver failure
    Patient trajectory and traversal rate
    Disease progression category Some or all aspects of the systems and methods described herein can be implemented in conjunction with the systems and methods as described in applicant's patents referenced hereinabove.

It may be advantageous to set forth definitions of certain words and phrases used in this patent document. The term "or" is inclusive, meaning and/or.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as methods or processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A system for increasing the overall survival for a liver disease patient, the system comprising:

a functional scanner configured to generate functional image data of a liver of the patient;

an image storage device in communication with the functional scanner, the image storage device being configured to receive and store the functional image data of the liver of the patient from the functional scanner;

a memory configured to store specific computer-executable instructions; and one or more hardware computer processors in communication with the memory and configured to execute the specific computer-executable instructions to at least:

receive the functional image data of the liver of the patient from the image storage device;

access patient information from a patient information database over a wireless or wire-like connection;

obtain parameters of a planned surgery or intervention, wherein the parameters include a margin volume indicative of functioning liver tissue to be eliminated during the planned surgery or intervention;

automatically process and analyze the functional image data to determine a functional liver volume, wherein the functional image data comprises a stack of transaxial functional images that includes healthy functional tissue, tumor tissue, and non-functional non-tumor tissue, and wherein processing and analyzing the functional image data comprises generating a combined image from the stack of transaxial functional images and determining a volume represented by the healthy functional tissue excluding the tumor tissue and non-functional non-tumor tissue in the combined image;

determine a pre-therapy liver functional reserve of the patient by determining a pre-therapy perfused hepatic mass index and a pre-therapy functional liver volume index;

determine a post-therapy liver functional reserve of the patient by determining a post-therapy perfused hepatic mass index and a post-therapy functional liver volume index;

determine a virulence of a liver disease of the patient;

determine a recommended dose escalation factor by constructing a virulence-reserve matrix comprising the liver disease virulence and pre-therapy and post-therapy liver functional data; and provide a recommended plan for treating liver disease comprising escalation of a treatment dose when the dose escalation factor is greater than one or de-escalation of a treatment dose when the dose escalation factor is less than one.

2. The system of claim 1, wherein the pre-therapy liver functional reserve is normalized by patient characteristics comprising one or more of gender, height, weight, age, biomarkers and genetic factors.

3. The system of claim 1, wherein the one or more computer hardware processors are further configured to determine a likelihood of post-therapy liver failure based on a comparison between the pre-therapy and post-therapy perfused hepatic mass indices and a comparison between the pre-therapy and post-therapy functional liver volume indices.

4. The system of claim 3, wherein the one or more computer hardware processors are further configured to determine a trajectory indicative of health of the patient based on a difference between the post-therapy perfused hepatic mass index and the post-therapy functional liver volume index.

5. The system of claim 4, wherein the one or more computer hardware processors are further configured to determine a traversal rate of the trajectory of the patient.

6. The system of claim 5, wherein the one or more computer hardware processors are further configured to update the post-therapy liver functional reserve based on the trajectory of the patient and the traversal rate of the trajectory.

7. The system of claim 1, wherein the patient receives treatment for the liver disease of the patient based on the dose escalation factor.

8. The system of claim 1, wherein the dose escalation factor is greater than one if the virulence is above a predetermined threshold and the post-therapy liver functional reserve is above a predetermined threshold, wherein the dose escalation factor is less than one if the virulence is below a predetermined threshold and the post-therapy liver functional reserve is below a predetermined threshold, wherein the dose escalation factor is one if the virulence is below a predetermined threshold and the post-therapy liver functional reserve is above a predetermined threshold, wherein the dose escalation factor is null if the virulence is above a predetermined threshold and the post-therapy liver functional reserve is below a predetermined threshold.

9. A system for treating a patient having a liver disease, the system comprising one or more computer hardware processors configured to at least:

receive functional image data of the liver of the patient that was generated by a functional scanner;

access patient information from a patient information database over a wireless or wire-like connection;

automatically process and analyze the functional image data to determine a functional liver volume (fLV), wherein the functional image data comprises a stack of transaxial functional images that includes healthy functional tissue, tumor tissue, and non-functional non-tumor tissue, and wherein processing and analyzing the functional image data comprises-generating a combined image from the stack of transaxial functional images and determining a volume represented by the healthy functional tissue excluding the tumor tissue and non-functional non-tumor tissue in the combined image;

determine a liver functional reserve (LFR) of the liver of the patient as a function of a product of at least two independent variables derived from the functional image data, the at least two independent variables comprising a quantitative liver function including a perfused hepatic mass (PHM) and the fLV; and provide a recommended plan for treating liver disease comprising escalating or de-escalating a treatment based on the LFR, wherein the treatment comprises radiation therapy, embolization, ablation, or surgical resection.

10. The system of claim 9, wherein the one or more computer hardware processors is further configured to determine a personalized dose value (PDV) based on the LFR and a virulence (V) of the liver disease.

11. The system of claim 10, wherein the one or more computer hardware processors is further configured to determine a dose escalation factor (DEF), wherein DEF=PDV/DN, in which DN is a radiation dose absorbed by non-tumor liver tissue of the patient.

12. The system of claim 9, wherein the one or more computer hardware processors is further configured to:

obtain parameters of a planned surgery or intervention;

determine the LFR of the liver of the patient pre-therapy;

determine, based on the pre-therapy LFR of the patient and the parameters of the planned surgery or intervention, a post-therapy LFR of the patient;

determine a virulence of a liver disease of the patient; and determine, based on the post-therapy LFR of the patient and the virulence of the liver disease of the patient, a recommended dose escalation factor.

13. A method for increasing the overall survival for a liver cancer patient, the method comprising:

automatically processing and analyzing functional image data to determine a functional liver volume (fLV), wherein the functional image data comprises a stack of transaxial functional images that includes healthy functional tissue, tumor tissue, and non-functional non-tumor tissue, and wherein processing and analyzing the functional image data comprises generating a combined image from the stack of transaxial functional images and determining a volume represented by the healthy functional tissue excluding the tumor tissue and non-functional non-tumor tissue in the combined image;

determining a liver functional reserve (LFR) of a liver of the patient as a function of at least two independent variables comprising a quantitative liver function including a perfused hepatic mass (PHM) and the fLV;

determining a dose escalation factor (DEF), wherein DEF=PDV/DN, in which PDV is a personalized dose value based on the LFR and DN is a radiation dose absorbed by non-tumor liver tissue of the patient; and treating a patient for liver cancer by escalating a radiation-treatment dose when the DEF is greater than 1 or de-escalating the radiation treatment dose when the DEF is less than 1.

14. The method of claim 13 further comprising determining the PDV based on a virulence (V) of the liver disease.

15. The method of claim 13 further comprising:

receiving an image of the liver of the patient from an image storage device;

accessing patient information from a patient information database over a wireless or wire-like connection;

obtaining parameters of a planned surgery or intervention;

determining the LFR of the liver of the patient pre-therapy, based on the image;

determining, based on the pre-therapy LFR of the patient and the parameters of the planned surgery or intervention, a post-therapy LFR of the patient;

determining a virulence of a liver disease of the patient; and determining, based on the post-therapy LFR of the patient and the virulence of the liver disease of the patient, the recommended DEF.

\* \* \* \* \*